(12) United States Patent
Kim et al.

(10) Patent No.: US 9,829,479 B2
(45) Date of Patent: Nov. 28, 2017

(54) PHOTOACOUSTIC IMAGING DEVICE AND OXYGEN SATURATION MEASUREMENT METHOD

(71) Applicant: POSTECH ACADEMY-INDUSTRY FOUNDATION, Pohang-si (KR)

(72) Inventors: Chul Hong Kim, Pohang-si (KR); Jee Hyun Kim, Daegu (KR); Min Yong Jeon, Daejoen (KR); Chang Ho Lee, Daegu (KR); Man-Sik Jeon, Daegu (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 259 days.

(21) Appl. No.: 14/640,422

(22) Filed: Mar. 6, 2015

(65) Prior Publication Data
US 2016/0003801 A1    Jan. 7, 2016

(30) Foreign Application Priority Data

Jul. 4, 2014    (KR) ........................ 10-2014-0083657

(51) Int. Cl.
*G01N 33/48* (2006.01)
*G01N 33/50* (2006.01)
*G01N 33/49* (2006.01)
*A61B 5/00* (2006.01)
*G02B 5/04* (2006.01)
(Continued)

(52) U.S. Cl.
CPC ....... *G01N 33/4925* (2013.01); *A61B 5/0095* (2013.01); *A61B 5/14551* (2013.01); *G01N 21/1702* (2013.01); *G01N 29/0654* (2013.01); *G01N 29/2418* (2013.01); *G01N 29/2425* (2013.01); *G02B 5/04* (2013.01);
(Continued)

(58) Field of Classification Search
None
See application file for complete search history.

(56) References Cited

U.S. PATENT DOCUMENTS 6,069,739 A * 5/2000 Borodovsky ........ G02B 3/0056
355/67

FOREIGN PATENT DOCUMENTS

KR    1020090088909    8/2009
KR    1020090116464    11/2009
KR    1020130033936    4/2013

OTHER PUBLICATIONS

English machine translation of KR 1020090116464, obtained on Feb. 13, 2017.*

(Continued)

*Primary Examiner* — Russell S Negin
(74) *Attorney, Agent, or Firm* — Cantor Colburn LLP

(57) ABSTRACT

Provided is a photoacoustic imaging device including: a light source unit which generates an ultra-broadband pulsed laser beam and outputs the ultra-broadband pulsed laser beam; a filter unit which filters narrowband pulsed laser beams having predetermined different wavelength bands from the ultra-broadband pulsed laser beam to selectively extract the narrowband pulsed laser beams and outputs the narrowband pulsed laser beams as pulsed laser beams for photoacoustic imaging; and a PA (photoacoustic) unit which receives the pulsed laser beams for photoacoustic imaging to irradiate a measurement object with the pulsed laser beams for photoacoustic imaging and receives photoacoustic signals generated from the measurement object.

14 Claims, 5 Drawing Sheets

(51) Int. Cl.
*A61B 5/1455* (2006.01)
*G01N 29/06* (2006.01)
*G01N 29/24* (2006.01)
*G01N 21/17* (2006.01)

(52) U.S. Cl.
CPC ............... *A61B 2562/0242* (2013.01); *G01N 2291/02466* (2013.01)

(56) References Cited

OTHER PUBLICATIONS

English machine translation of KR 1020130033936, obtained on Feb. 13, 2017.*
Lee et al. Combined phtoacoustic and optical coherence tomography using a single near-infrared supercontinuum laser source. Applied Optics, Mar. 13, 2013, vol. 52, pp. 1824-1828.*
Jeon et al. Pulse-amplitude-equalized output from a rational harmonic mode-locked fiber laser. Optics Letters, 1998, vol. 23, pp. 855-857.*

* cited by examiner

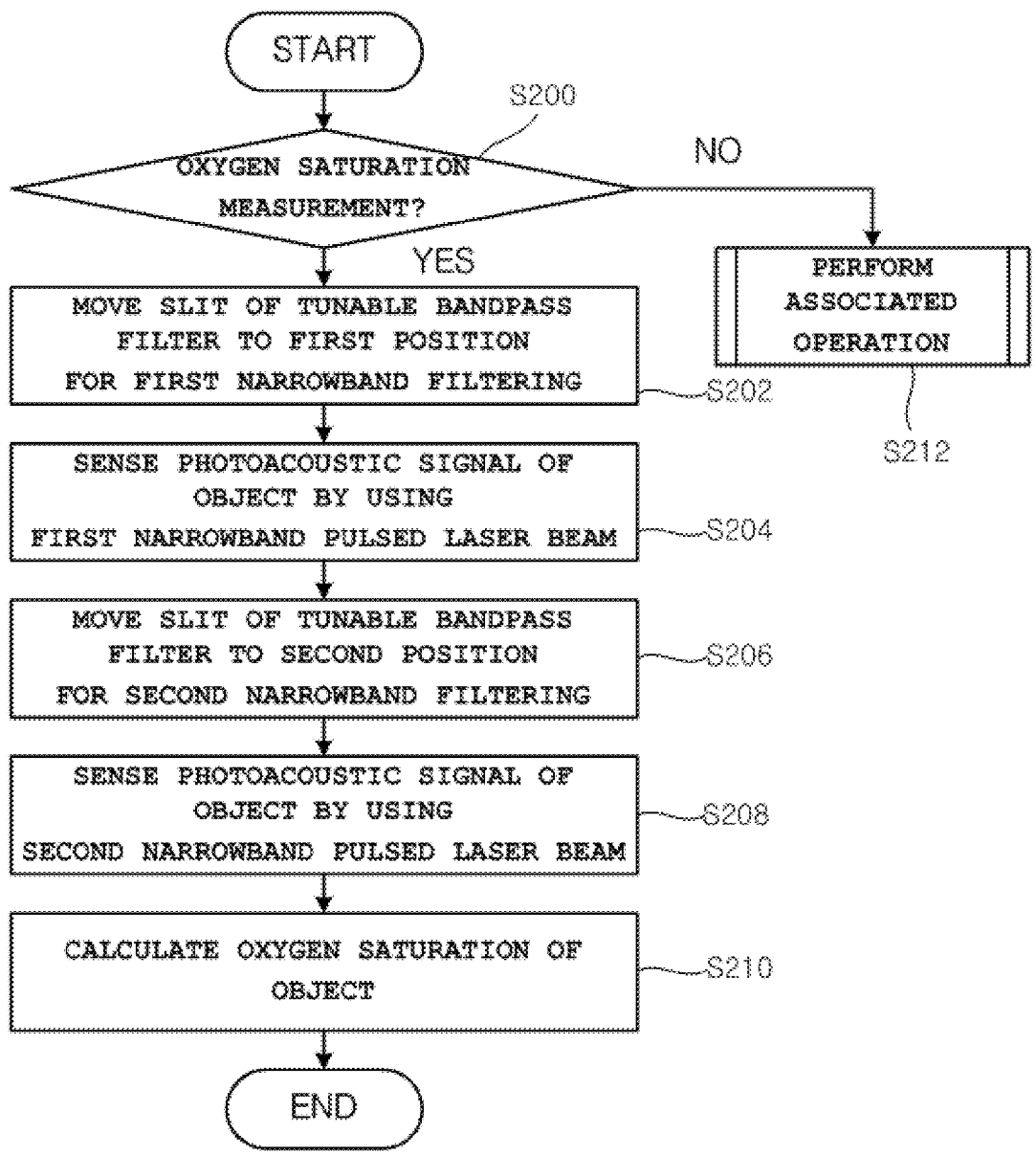

PHOTOACOUSTIC IMAGING DEVICE AND OXYGEN SATURATION MEASUREMENT METHOD

CROSS-REFERENCE TO RELATED PATENT APPLICATION

This application claims the benefit of Korean Patent Application No. 10-2014-0083657, filed on Jul. 4, 2014 in the Korean Intellectual Property Office, the disclosure of which is incorporated herein in its entirety by reference.

BACKGROUND OF THE INVENTION

1. Field of the Invention

The present invention relates to a photoacoustic imaging technique, and more particularly, to a photoacoustic imaging device for filtering two narrowband pulsed laser beams having different wavelength bands from an ultra-broadband pulsed laser beam generated from one light source by a compact, inexpensive mechanical filter to selectively extract the two narrowband pulsed laser beams and measuring oxygen saturation of a measurement object such as a living tissue by using the extracted narrowband pulsed laser beams and an oxygen saturation measurement system using the photoacoustic imaging device.

2. Description of the Related Art

In general, in a living tissue, lesion may be aggravated due to various causes. As the lesion is aggravated, the structure AC00 of the living tissue is changed, or oxygen saturation of inside of structure is also changed.

In order to check the state of the living tissue, an ultrasonic diagnosis method has been used in the related art. In this ultrasonic diagnosis method, the living tissue is irradiated with an ultrasonic wave, and the reflected wave is measured, so that the state of the living tissue is checked. However, due to absorption of a portion of the ultrasonic wave by the living tissue, and thus, the reflected wave is not properly generated. Therefore, there is a problem of low resolution.

In order to solve the problem of low resolution of the ultrasonic diagnosis method, an X-ray diagnosis apparatus may be utilized. However, there is a problem in that the living tissue is exposed to X-ray.

Therefore, there has been required a technique which is harmless to a human body and is able to acquire an accurate, high-resolution image and oxygen saturation of the living tissue. Herein, the oxygen saturation is a percentage of a concentration of oxygenated hemoglobin to a concentration of total hemoglobin inside the tissue.

A technique for complying with this requirement is disclosed in Korean Patent Application Laid-Open No. 10-2013-0033936, titled as "A Photoacoustic Imaging Device Using Near-Infrared Laser".

The Patent Document discloses a photoacoustic imaging device using a near-infra red laser, including: a probe; a laser emitting unit which is installed in the probe to emit a laser beam with which a living tissue is irradiated; a transducer which is installed to sense an ultrasonic wave instantaneously generated from the living tissue which is irradiated with the laser due to thermal elastic expansion; and a controller which generates a photoacoustic image and an oxygen saturation distribution of the living tissue by using the ultrasonic wave sensed by the transducer and performs a mapping between the generated photoacoustic imaging of the living tissue and the oxygen saturation distribution.

Particularly, the laser emitting unit emits two or more different narrowband laser beams.

The two or more narrowband laser beams having different wavelengths are used due to the following reasons.

In general, in measurement of oxygen saturation in blood, two or more narrowband pulsed laser beams are incident on blood, and a concentration of oxygenated blood and a concentration of deoxygenated blood are calculated by using intensities of photoacoustic signals generated wavelength by wavelength and optical absorption coefficients.

However, in order to generate the two or more narrowband pulsed laser beams from one light source, high expensive, complex optical systems such as an OPO (optical parametric oscillator), a dye laser, or a Ti:sapphire laser are required. Accordingly, there is a problem in that the photoacoustic imaging device is highly expensive.

As cited literatures, there are Korean Patent Application Laid-Open Nos. 10-2013-0033936 and 10-2009-0088909.

SUMMARY OF THE INVENTION

The present invention is to provide a photoacoustic imaging device for filtering two narrowband pulsed laser beams having different wavelength bands from an ultra-broadband pulsed laser beam generated from one light source by a compact, inexpensive mechanical filter to selectively extract the two narrowband pulsed laser beams and measuring oxygen saturation of a living tissue by using the two narrowband pulsed laser beams and an oxygen saturation measurement system using the photoacoustic imaging device.

According to an aspect of the present invention, there is provided a photoacoustic imaging device including: a light source unit which generates an ultra-broadband pulsed laser beam and outputs the ultra-broadband pulsed laser beam; a filter unit which filters narrowband pulsed laser beams having predetermined different wavelength bands from the ultra-broadband pulsed laser beam to selectively extract the narrowband pulsed laser beams and outputs the narrowband pulsed laser beams as pulsed laser beams for photoacoustic imaging; and a PA (photoacoustic) unit which receives the pulsed laser beams for photoacoustic imaging to irradiate a measurement object with the pulsed laser beams for photoacoustic imaging and receives photoacoustic signals generated from the measurement object. The measurement object may include a living tissue.

According to the present invention, two pulsed laser beams for photoacoustic imaging having different wavelength band required for a photoacoustic imaging device measuring oxygen saturation of a measurement object such as a living tissue can be allowed to be simply generated at a low cost, and thus, the price of the photoacoustic imaging device is lowered, so that it is possible to improve competitiveness in the market.

BRIEF DESCRIPTION OF THE DRAWINGS

The above and other features and advantages of the present invention will become more apparent by describing in detail exemplary embodiments thereof with reference to the attached drawings in which:

FIG. 3 is a flowchart illustrating an oxygen saturation measurement method according to another exemplary embodiment of the present invention.

DETAILED DESCRIPTION OF THE INVENTION

Figure 1:
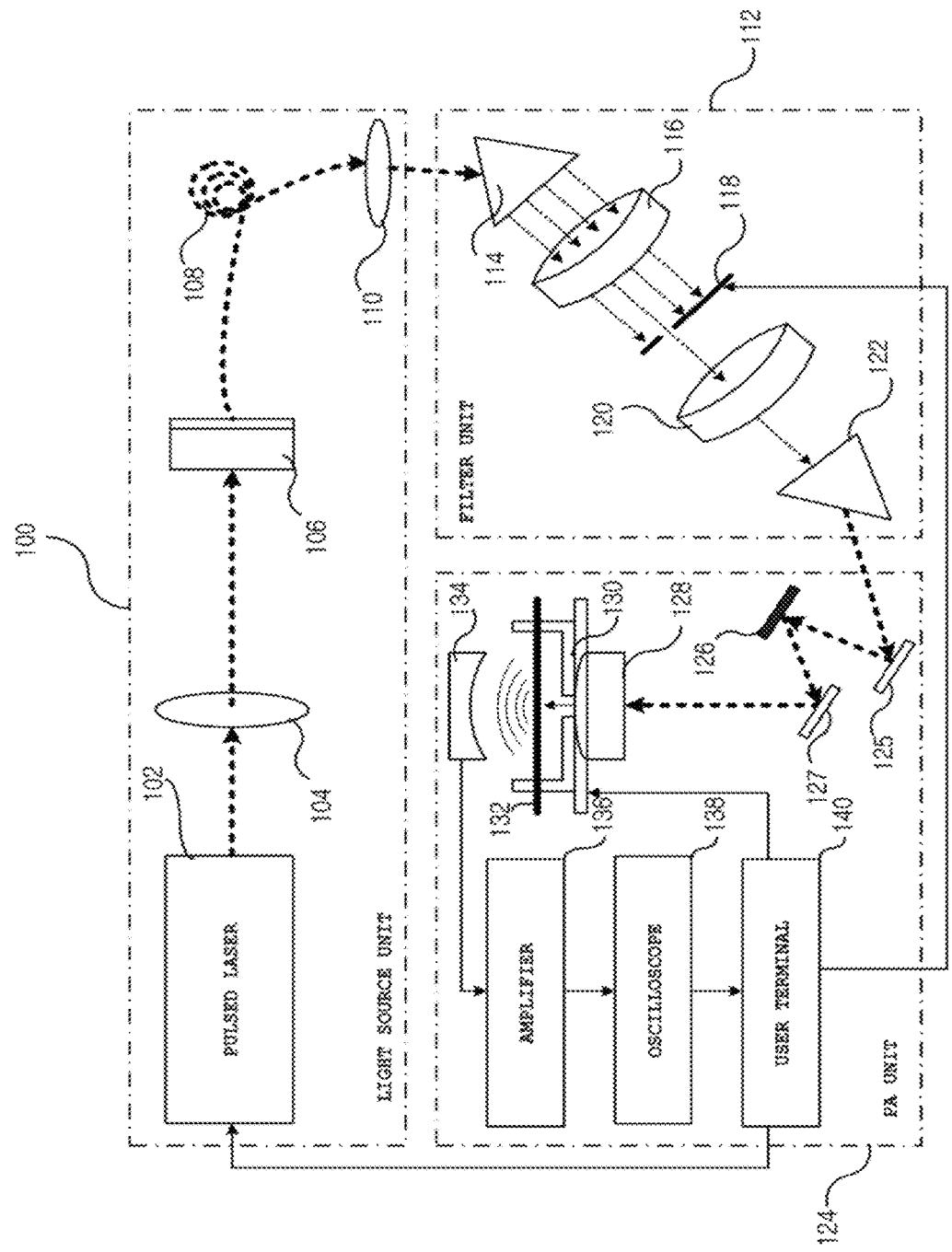
FIG. 1 is a diagram illustrating a configuration of a photoacoustic imaging device according to an exemplary embodiment of the present invention.

In the present invention, oxygen saturation is measured based on a photoacoustic signal generated by using an ultra-broadband pulsed laser as a light source.

More specifically, in a photoacoustic imaging device according to the present invention, two narrowband pulsed laser beams having different wavelength bands are extracted from an ultra-broadband pulsed laser beam by using a mechanical filter, and the extracted narrowband pulsed laser beams are incident on an object (hereinafter, referred to as a measurement object) which is to be measured. The measurement object receives and absorbs energy of the two narrowband pulsed laser beams, so that photoacoustic signals corresponding to the two narrowband pulsed laser beams are generated due to the photoacoustic effect. Herein, the measurement object may include a living tissue such as blood.

At this time, the photoacoustic imaging device measures the respective photoacoustic signals as voltage values corresponding to the two narrowband pulsed laser beams by using an ultrasonic transducer. Since the intensity of the photoacoustic signal has a linear relationship with an optical absorption coefficient of the measurement object, the intensity thereof can be treated as an optical absorption coefficient.

The photoacoustic imaging device measures a relative concentration between oxygenated blood and deoxygenated blood by using the intensities of the photoacoustic signals corresponding to the two narrowband pulsed laser beams and the optical absorption coefficients (sometimes, referred to as molar extinction coefficients) and calculates the oxygen saturation in blood according to the following Mathematical Formulas 1 to 4.

[Mathematical Formula 1]
$$[C_{oxy-B}] = \frac{1}{\ln} \cdot \frac{\varepsilon_{deoxy-B}(\lambda_{b2})\mu_a(\lambda_{b1}) - \varepsilon_{deoxy-B}(\lambda_{b1})\mu_a(\lambda_{b2})}{\varepsilon_{deoxy-B}(\lambda_{b2})\varepsilon_{oxy-B}(\lambda_{b1}) - \varepsilon_{deoxy-B}(\lambda_{b1})\varepsilon_{oxy-B}(\lambda_{b2})}$$

[Mathematical Formula 2]
$$[C_{deoxy-B}] = \frac{1}{\ln} \cdot \frac{\varepsilon_{oxy-B}(\lambda_{b1})\mu_a(\lambda_{b2}) - \varepsilon_{oxy-B}(\lambda_{b2})\mu_a(\lambda_{b1})}{\varepsilon_{deoxy-B}(\lambda_{b2})\varepsilon_{oxy-B}(\lambda_{b1}) - \varepsilon_{deoxy-B}(\lambda_{b1})\varepsilon_{oxy-B}(\lambda_{b2})}$$

[Mathematical Formula 3]
$$[C_{HbT}] = [C_{oxy-B}] + [C_{deoxy-B}]$$

[Mathematical Formula 4]
$$[SO_2] = \frac{[C_{oxy-B}]}{[C_{oxy-B}] + [C_{deoxy-B}]}$$

Herein, in Mathematical Formulas 1 to 4, $[C_{oxy-B}]$ denotes a concentration of oxygenated blood, $[C_{deoxy-B}]$ denotes deoxygenated blood, $[C_{HbT}]$ denotes a concentration of hemoglobin, and $[SO_2]$ denotes a concentration of oxygen in blood. $\lambda_{b1}$ and $\lambda_{b2}$ denote narrow wavelength bands, and $\varepsilon_{oxy-B}(\lambda_{b1})$ and $\varepsilon_{deoxy-B}(\lambda_{b1})$ denote optical absorption coefficients of pure oxygenated blood and deoxygenated blood acquired by using a $\lambda_{b1}$ narrowband laser. $\varepsilon_{oxy-B}(\lambda_{b2})$ and $\varepsilon_{deoxy-B}(\lambda_{b2})$ denote optical absorption coefficients of pure oxygenated blood and deoxygenated blood acquired by using a $\lambda_{b2}$ narrowband laser. $\mu_a(\lambda_{b1})$ denotes an optical absorption coefficient of $\lambda_{b1}$, and $\mu_a(\lambda_{b2})$ denotes an optical absorption coefficient of $\lambda_{b2}$.

According to the present invention, two narrowband pulsed laser beams having different wavelength bands are filtered from an ultra-broadband pulsed laser beam generated from one light source by a compact, inexpensive mechanical filter to selectively extract the two narrowband pulsed laser beams, and oxygen saturation is measured by using the extracted narrowband pulsed laser beams. Therefore, the price of the photoacoustic imaging device is lowered, so that it is possible to improve competitiveness in the market.

<Configuration of Photoacoustic Imaging Device>

A configuration of a photoacoustic imaging device according to an exemplary embodiment of the present invention will be described with reference to FIG. 1.

The photoacoustic imaging device is configured to include a light source unit 100, a filter unit 112, and a photoacoustic (PA) unit 124.

The light source unit 100 of the photoacoustic imaging device generates and outputs an ultra-broadband pulsed laser beam.

The light source unit 100 is configured to include a pulsed laser 102, an eyepiece lens (AL) 104, an objective lens (OL) 106, a photonic crystal fiber (PCF) 108, and a collimator (CM) 110.

The pulsed laser 102 generates a single wavelength pulsed laser beam to supply the single wavelength pulsed laser beam to the eyepiece lens 104 and the objective lens 106. The pulsed laser 102 may be configured with a 1064 nm microchip Nd:YAG laser.

The eyepiece lens 104 and the objective lens 106 transform the single wavelength pulsed laser beam supplied from the pulsed laser so as to have a predetermined form and supplies the transformed single wavelength pulsed laser beam to the photonic crystal fiber 108. The photonic crystal fiber 108 converts the single wavelength pulsed laser beam into an ultra-broadband pulsed laser beam due to non-linear phenomenon and supplies the ultra-broadband pulsed laser beam to the collimator 110. The collimator 110 collimates the ultra-broadband pulsed laser beam output from the photonic crystal fiber 108 so as to have a predetermined beam size and supplies the collimated ultra-broadband pulsed laser beam to the filter unit 112.

The filter unit 112 filters two narrowband pulsed laser beams having different wavelength bands from the ultra-broadband pulsed laser beam to selectively extract two narrowband pulsed laser beams according to a command of a user terminal 140 and outputs the extracted narrowband pulsed laser beams as pulsed laser beams for photoacoustic imaging. The above-described filter unit 112 is configured to include a first prism (EP) 114, a first lens (CL) 116, a tunable bandpass filter (TB filter) 118, a second lens 120, and a second prism 122.

The first prism 114 separates the ultra-broadband pulsed laser beam wavelength by wavelength to supply the wavelength-by-wavelength-separated ultra-broadband pulsed laser beam to the first lens 116.

The first lens 116 is configured to have a cylindrical shape, and the wavelength-by-wavelength-separated ultra-broadband pulsed laser beam is incident from the first prism. The first lens 116 adjusts the irradiation angle of the incident ultra-broadband pulsed laser beam to be perpendicular to the incident surface of the tunable bandpass filter 118, so that the ultra-broadband pulsed laser beam is perpendicularly incident on the incident surface of the tunable bandpass filter 118. The tunable bandpass filter 118 includes a mechanical slit of which position is changeable according to a command of the user terminal 140 to selectively extract the two narrowband pulsed laser beams having different wavelength bands required for oxygen saturation measurement from the ultra-broadband pulsed laser beam.

In order to extract the two narrowband pulsed laser beams from the wavelength-by-wavelength-separated ultra-broadband pulsed laser beam, the slit is moved to the positions corresponding to the irradiation areas of the two narrowband pulsed laser beams. Therefore, the narrowband pulsed laser beams can be selectively filtered (extracted) and output. The tunable bandpass filter 118 having a slit of which position is changeable is disclosed in Korean Patent Application Laid-Open No. 10-2009-116464 (titled as "Wavelength Tunable Laser Using Rotation Slit", published on Nov. 11, 20009), and thus, detailed description thereof is omitted.

Figure 2:
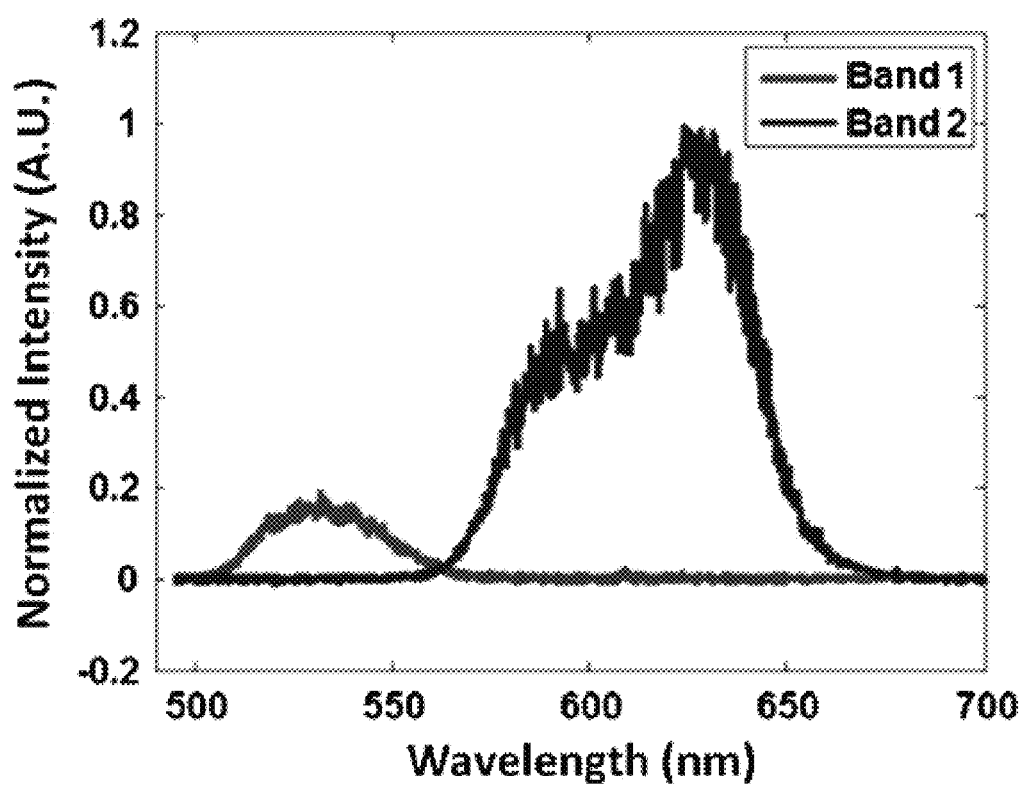
FIG. 2 is a graph illustrating spectra of narrowband pulsed laser beams filtered by a tunable bandpass filter wavelength by wavelength according to the exemplary embodiment of the present invention.

Due to the changeable position of the slit, the tunable bandpass filter 118 selectively passes the two narrowband pulsed laser beams having wavelength bands required for the oxygen saturation measurement to selectively extract and output the two or more narrowband pulsed laser beams. FIG. 2 is a graph illustrating spectra of the narrowband pulsed laser beams extracted by the tunable bandpass filter 118 wavelength by wavelength. This figure collectively illustrates a spectrum of the narrowband pulsed laser beam of a first band (band 1) corresponding to a first narrow band and a spectrum of the narrowband pulsed laser beam of a second band (band 2) corresponding to a second narrow band.

The two narrowband pulsed laser beams passing through the tunable bandpass filter 118 are incident on the second lens 120.

The second lens 120 is configured to have a cylindrical shape, and the two narrowband pulsed laser beams having different wavelength bands are sequentially incident from the tunable bandpass filter. The second lens 120 adjusts the irradiation angle of the two incident narrowband pulsed laser beams to be perpendicular to the incident surface of the second prism 122, so that the two narrowband pulsed laser beams is perpendicularly incident on the incident surface of the second prism 122.

The second prism 122 combines the two wavelength-by-wavelength-separated incident narrowband pulsed laser beams wavelength by wavelength to generate a pulsed laser beam for photoacoustic imaging and supplies the pulsed laser beam for photoacoustic imaging to the PA unit 124.

The PA unit 124 irradiates the measurement object with the pulsed laser beam for photoacoustic imaging and senses the oxygen saturation by measuring and processing a photoacoustic signal emitted from the measurement object which absorbs the pulsed laser beam for photoacoustic imaging. The measurement object includes a living tissue such as blood.

The PA unit 124 is configured to include first and second mirrors (M) 125 and 127, a scanner 126, an objective lens (OL) 128, a linear stage (LS) 130, a tube (TU) 132, an ultrasonic transducer (TX) 134, an amplifier 136, an oscilloscope 138, and a user terminal 140.

The first mirror 125 reflects the pulsed laser beam for photoacoustic imaging input from the filter unit 112 toward the scanner 126.

The scanner 126 changes a transmission path of the pulsed laser beam for photoacoustic imaging to guide the pulsed laser beam for photoacoustic imaging into the living tissue 132. As the scanner 126, a galvo scanner, an MEMS scanner, or the like may be selectively employed.

The second mirror 126 reflects the pulsed laser beam for photoacoustic imaging input from the scanner 126 toward the objective lens 128.

The objective lens 128 is focused on the tube 132 where the measurement object is accommodated, so that the pulsed laser beam for photoacoustic imaging is focused to be incident on the measurement object accommodated in the tube 132. The tube 132 is disposed over the linear stage 130, and the position of the tub 132 is changed according to user's command transmitted from the user terminal 140.

The tube 132 accommodates the measurement object, for example, a living tissue such as blood, and the measurement object absorbs the pulsed laser beams for photoacoustic imaging corresponding to the two narrowband pulsed laser beams and generates the corresponding photoacoustic signals. The ultrasonic transducer 134 receives the photoacoustic signal generated by the measurement object injected into the tube 132 to generate a measurement signal and supplies the measurement signal to the amplifier 136.

The amplifier 136 amplifies the measurement signal and supplies the amplified measurement signal to the oscilloscope 138. The oscilloscope 138 or a data acquisition device such as a DAQ board or a digitizer converts the measurement signal of the amplifier 136 into a digital signal and supplies the digital signal to the user terminal 140.

The user terminal 140 is a processing unit such as a computer. If oxygen saturation measurement is requested, the user terminal allows the slit of the tunable bandpass filter 118 to be moved so that the pulsed laser beams for photoacoustic imaging corresponding to the two narrowband pulsed laser beams are input to the measurement object. The user terminal receives the measurement signal and performs Hilbert transform and envelop detection to acquire the intensities of the measurement signals. The user terminal stores the acquired intensities of the measurement signals and calculates measurement values of oxygen saturation based on the above-described Mathematical Formulas 1 to 4 by using the stored measurement values. The user terminal displays the calculated measurement values of oxygen saturation to inform the user.

<Oxygen Saturation Measurement Method>

Next, an oxygen saturation measurement system according to an exemplary embodiment of the present invention will be described in detail with reference to FIG. 3.

If oxygen saturation measurement is requested by a user, the user terminal 140 supplies a command of moving the slit of the tunable bandpass filter 118 to the first position for first narrowband filtering to the tunable bandpass filter 118 (step 202). According to the command of the user terminal 140, the tunable bandpass filter 118 moves the slit to the first position, so that the first narrowband pulsed laser beam is filtered. The first narrowband pulsed laser beam is converted into the pulsed laser beam for photoacoustic imaging to be incident on the measurement object.

The user terminal 140 receives photoacoustic signal sensing information generated from the measurement object on which the pulsed laser beam for photoacoustic imaging is incident (step 204).

Next, the user terminal 140 supplies a command of moving the slit of the tunable bandpass filter to the second position for the second narrowband filtering to the tunable bandpass filter 118 (step 206). According to the command of the user terminal 140, the tunable bandpass filter 118 moves the slit to the second position, so that the second narrowband pulsed laser beam is filtered. The second narrowband pulsed laser beam is converted into the pulsed laser beam for photoacoustic imaging to be incident on the measurement object.

The user terminal 140 receives photoacoustic signal sensing information generated from the measurement object on which the pulsed laser beam for photoacoustic imaging is incident (step 208).

Next, the user terminal 140 calculates the oxygen saturation of the measurement object by using Mathematical Formulas 1 to 4 (step 210).

Results of the measurement of the oxygen saturation by the photoacoustic imaging device according to the exemplary embodiment of the present invention will be described with reference to FIGS. 4A to 4D.

Fresh oxygenated bovine blood and deoxygenated bovine blood were mixed at predetermined rates of 10%, 20%, 40%, 60%, 80%, and 100%. Next, within a short time, oxygen saturation was measured by using the photoacoustic imaging device according to the present invention. The results of the measurement are illustrated in FIGS. 4A to 4D.

Figure 4A:
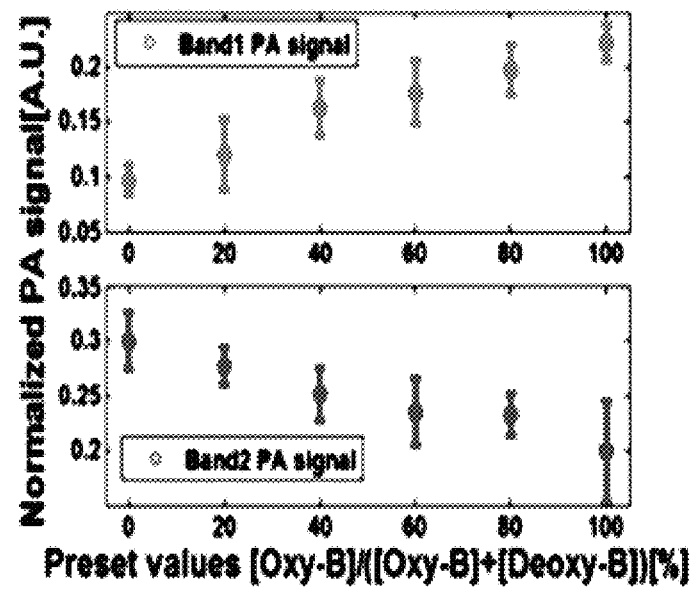
FIGS. 4A to 4D are graphs illustrating results of measurement of oxygen saturation according to the exemplary embodiment of the present invention.

FIG. 4A illustrates PA signals measured by the photoacoustic imaging device according to the embodiment of the present invention. The result (BAND1 PA signal) of the measurement using the first single wavelength pulsed laser beam is increased as the concentration of oxygen is increased, and the result of (BAND2 PA signal) of the measurement using the second single wavelength pulsed laser beam is decreased as the concentration of oxygen is increased.

Figure 4B:
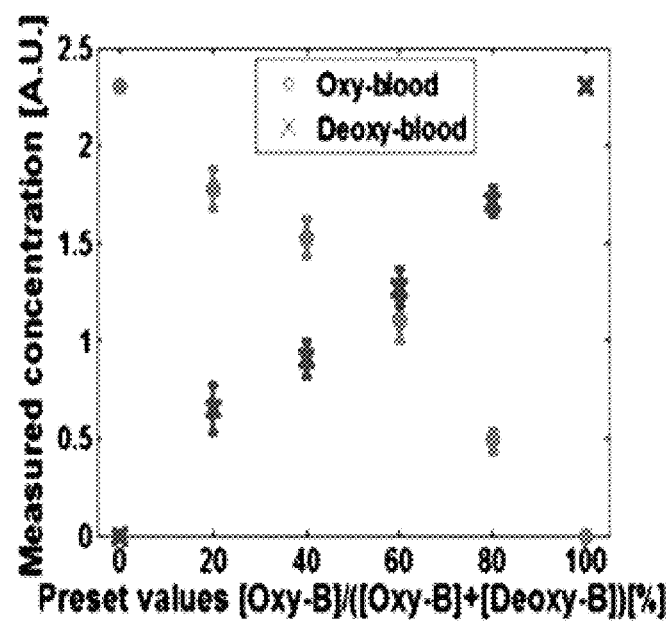
Figure 4C:
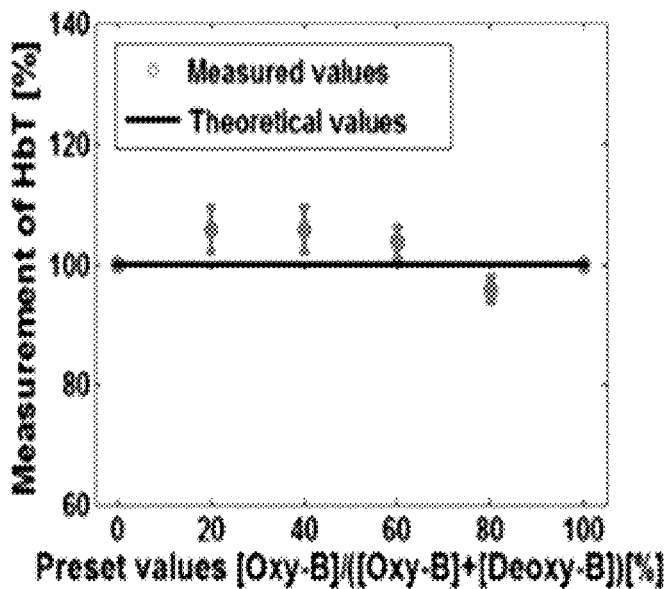

FIG. 4B illustrates concentrations of the oxygenated blood and the deoxygenated blood calculated by using the PA signals of FIG. 4A. FIG. 4C illustrates the concentration of hemoglobin. As illustrated in FIG. 4C, the values of the measurement by the photoacoustic imaging device according to the present invention are substantially coincident with theoretical values.

Figure 4D:
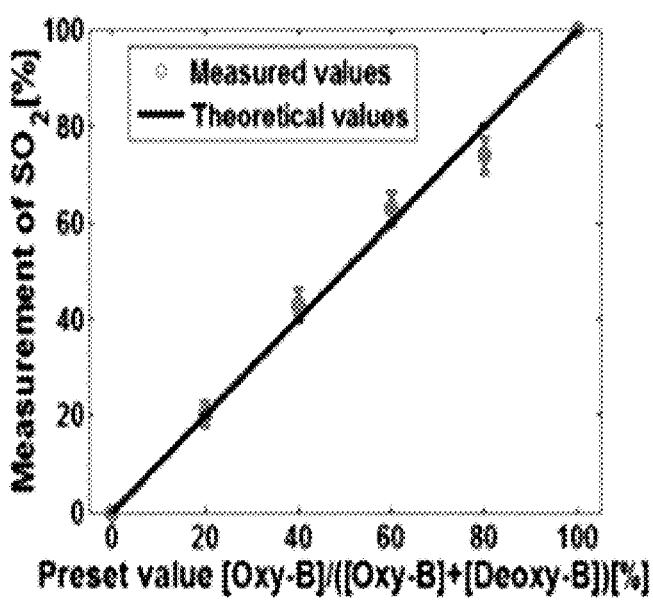

FIG. 4D illustrates the oxygen saturation measured by using the values of FIGS. 4A to 4C. As illustrated in FIG. 4D, the values of the measurement by the photoacoustic imaging device according to the present invention are substantially coincident with theoretical values.

In the exemplary embodiments of the present invention, the photonic crystal fiber is employed to convert the pulsed laser beam into the ultra-broadband pulsed laser beam. However, a broadband pulsed dye laser may be employed by the present invention, which is obvious to the ordinarily skilled in the related art. In addition, a program embodying the method according to the present invention may be recorded on a computer readable recording medium, which is obvious to the ordinarily skilled in the related art. While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:

1. A photoacoustic imaging device comprising:
  a light source unit which generates an ultra-broadband pulsed laser beam and outputs the ultra-broadband pulsed laser beam;
  a filter unit which filters narrowband pulsed laser beams having predetermined different wavelength bands from the ultra-broadband pulsed laser beam to selectively extract the narrowband pulsed laser beams and outputs the narrowband pulsed laser beams as pulsed laser beams for photoacoustic imaging; and
  a PA (photoacoustic) unit which receives the pulsed laser beams for photoacoustic imaging to irradiate a measurement object with the pulsed laser beams for photoacoustic imaging, receives photoacoustic signals generated from the measurement object, processes the received photoacoustic signals to detect an oxygen saturation of the measurement object, and outputs the oxygen saturation of the measurement object,
  wherein the filter unit includes:
    a first prism which receives the ultra-broadband pulsed laser beam as an input, separates the ultra-broadband pulsed laser beam wavelength by wavelength, and emits the ultra-broadband pulsed laser beam;
    a tunable bandpass filter which includes a slit of which position is changeable, selectively filters the narrowband pulsed laser beams by using the slit, and emits the narrowband pulsed laser beams; and
    a second prism which receives the narrowband pulsed laser beam emitted from the tunable bandpass filter, generates the pulsed laser beams for photoacoustic imaging, and emits the pulsed laser beams for photoacoustic imaging, and
  wherein the position of the slit of the tunable bandpass filter is changed so as to correspond to incident positions of the narrowband pulsed laser beams.

2. The photoacoustic imaging device according to claim 1, wherein the light source unit includes:
  a pulsed laser which generates a pulsed laser beam; and
  an optical output unit which receives the pulsed laser beam as an input, converts the pulsed laser beam into the ultra-broadband pulsed laser beam, and emits the ultra-broadband pulsed laser beam.

3. The photoacoustic imaging device according to claim 2, wherein the light source unit further includes a collimating lens which collimates the ultra-broadband pulsed laser beam supplied from the optical output unit and supplies the collimated ultra-broadband pulsed laser beam to the filter unit.

4. The photoacoustic imaging device according to claim 1, wherein the filter unit further includes a lens which changes an optical path of the pulsed laser beam emitted from the first prism so that the pulsed laser beam is perpendicularly incident on an incident surface of the tunable bandpass filter.

5. The photoacoustic imaging device according to claim 1, wherein the filter unit further includes a lens which changes optical paths of the narrowband pulsed laser beams emitted from the tunable bandpass filter so that the narrowband pulsed laser beams are perpendicularly incident on an incident surface of the second prism.

6. The photoacoustic imaging device according to claim 1, wherein the PA unit includes:
  a stage where the measurement object is disposed;
  a mirror which reflects the supplied pulsed laser beam for photoacoustic imaging to supply the pulsed laser beam for photoacoustic imaging toward the measurement object;
  an objective lens which is located between the mirror and the stage to focus the pulsed laser beam for photoacoustic imaging and supply the pulsed laser beam for photoacoustic imaging toward the measurement object;
  an ultrasonic transducer which receives the photoacoustic signal generated by the measurement object and outputs the photoacoustic signal;
  an amplifier which amplifies the photoacoustic signal output from the ultrasonic transducer and supplies the amplified photoacoustic signal;

an oscilloscope which processes the amplified photoacoustic signal and outputs the processed photoacoustic signal; and a user terminal which processes the photoacoustic signal supplied by the oscilloscope and outputs the processed photoacoustic signal and which supplies a control command so that the position of the stage is changed according to user's request.

7. The photoacoustic imaging device according to claim 1, wherein the PA unit further includes a scanner which is located on a transmission path of the pulsed laser beam for photoacoustic imaging between the mirror and the measurement object to guide the pulsed laser beam for photoacoustic imaging into the measurement object.

8. An oxygen saturation measurement system using a photoacoustic imaging device, comprising:

generating an ultra-broadband pulsed laser beam;

filtering narrowband pulsed laser beams having predetermined different wavelength bands from the ultra-broadband pulsed laser beam to selectively extract the narrowband pulsed laser beams, converting the narrowband pulsed laser beams into pulsed laser beams for photoacoustic imaging, and outputting the pulsed laser beams for photoacoustic imaging;

irradiating a measurement object with the pulsed laser beams for photoacoustic imaging; and receiving photoacoustic signals generated by the measurement object which absorbs the pulsed laser beams for photoacoustic imaging and calculating oxygen saturation by using the received photoacoustic signals, wherein the filtering the narrowband pulsed laser beams includes:

receiving the ultra-broadband pulsed laser beam, separating the ultra-broadband pulsed laser beam wavelength-by-wavelength, and emitting the separated ultra-broadband pulsed laser beam extracting the two narrowband pulsed laser beams having different wavelength bands required for oxygen saturation measurement from the ultra-broadband pulsed laser beam and emitting the narrowband pulsed laser beams; and converting the emitted narrowband pulsed laser beams into pulsed laser beams for photoacoustic imaging by using a prism, wherein a tunable bandpass filter including a slit of which position is changeable is used to extract the two narrowband pulsed laser beams from the ultra-broadband pulsed laser beam, and the position of the slit of the tunable bandpass filter is changed so as to correspond to incident positions of the two narrowband pulsed laser beams.

9. The oxygen saturation measurement system according to claim 8, wherein the generating the ultra-broadband pulsed laser beam includes:

generating the pulsed laser beam; and converting the pulsed laser beam into the ultra-broadband pulsed laser beam.

10. The oxygen saturation measurement system according to claim 9, wherein the generating the ultra-broadband pulsed laser beam further includes collimating the ultra-broadband pulsed laser beam and outputting the ultra-broadband pulsed laser beam.

11. The oxygen saturation measurement system according to claim 8, wherein the filtering the narrowband pulsed laser beams further includes changing an optical path of the wavelength-by-wavelength-separated pulsed laser beam by using a lens so that the pulsed laser beam is perpendicularly incident on an incident surface of the tunable bandpass filter.

12. The oxygen saturation measurement system according to claim 8, wherein the filtering the narrowband pulsed laser beams further includes changing optical paths of the narrowband pulsed laser beams by using a lens so that the narrowband pulsed laser beams are perpendicularly incident on a surface of the prism.

13. The oxygen saturation measurement system according to claim 8, wherein the receiving the photoacoustic signals includes:

receiving the photoacoustic signal generated by the measurement object;

amplifying the received photoacoustic signal; and processing the amplified photoacoustic signal and calculating oxygen saturation.

14. The oxygen saturation measurement system according to claim 8, further comprising guiding a transmission path of the pulsed laser beam for photoacoustic imaging input to the measurement object by using a scanner.

* * * * *